(12) United States Patent
Solanky et al.

(10) Patent No.: US 6,916,960 B2
(45) Date of Patent: Jul. 12, 2005

(54) DIOL-FUNCTIONALIZED ANTIOXIDANT AND PROCESS FOR PREPARATION THEREOF

(75) Inventors: Shailendra Singh Solanky, Pune (IN); Shrojal Mohitkumar Desai, Pune (IN); Raj Pal Singh, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,126

(22) Filed: Mar. 25, 2003

(65) Prior Publication Data

US 2004/0192969 A1 Sep. 30, 2004

(51) Int. Cl.[7] .................. C07C 215/50; C07C 213/02
(52) U.S. Cl. ........................ 564/355; 564/360
(58) Field of Search .................. 564/355, 360

(56) References Cited

PUBLICATIONS

Database CAPLUS on STN, Acc. No. 1968:402701, Bruk et al., SU 192215, Feb. 6, 1967 (abstract).*
Database CASREACT on STN, Acc. No. 58:66202, Ershov et al., Izvestiya Akademii Nauk SSSR, Seriya Khimicheskaya (1962), p. 2015–22 (abstract).*
Bruk et al., Izvestiya Akademii Nauk SSSR, Seriya Khimicheskaya (1962), p. 2015–22.*
English translation of Bruk et al., Izvestiya Akademii Nauk SSSR, Seriya Khimicheskaya (1962), p. 2015–22.*

* cited by examiner

*Primary Examiner*—Brian Davis
(74) *Attorney, Agent, or Firm*—Ladas & Parry

(57) ABSTRACT

Diol-functionalized antioxidants and the process for the preparation thereof are disclosed and have the general formula (I):

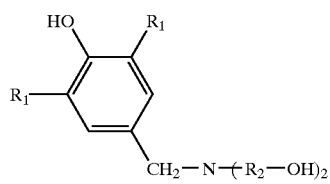

Formula (I)

wherein:
$R_1$ is tert-butyl and $R_2$ is $C_1$ to $C_8$ linear or branched alkyl. The invention also pertains to a process for their preparation.
Which comprises:
Reacting a halo functionalized antioxidant having the general formula (II):

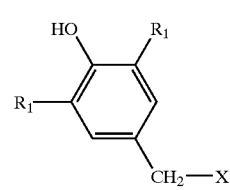

Formula (II)

wherein:
$R_1$ is tert-butyl and X is bromide (Br) with a diol having general formula (IV):

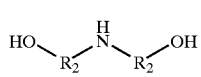

Formula (IV)

wherein
$R_2$ is $C_1$ to $C_8$ linear or branched alkyl.

9 Claims, No Drawings

DIOL-FUNCTIONALIZED ANTIOXIDANT AND PROCESS FOR PREPARATION THEREOF

FIELD OF THE INVENTION

The present invention relates to a novel antioxidant based on functionalized hindered phenol and the process for the preparation thereof. More particularly it relates to the compounds of formula I:

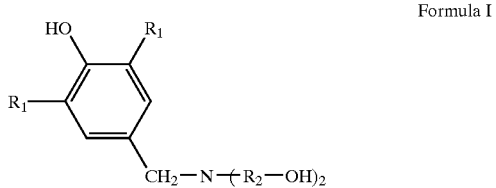

Formula I wherein $R_1$ is tert-butyl and $R_2$ is $C_1$ to $C_8$ linear or branched alkyl. More particularly the present invention relates to a process of preparation of a antioxidant using compound of formula II:

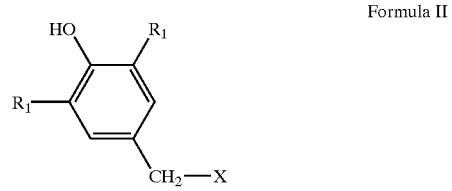

Formula II wherein $R_1$ is a tertiary butyl group and X is Br, which is prepared by the free radical bromination of compound having general Formula (III):

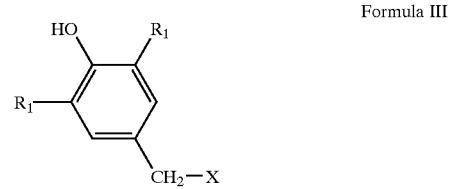

Formula III wherein $R_1$ is a tertiary butyl group and X is hydrogen (H).

The invention also relates to synthesis of diol derivatives of conventional hindered phenol antioxidants and useful as condensable monomer for synthesis of many polymers with in-built antioxidants and the process for the synthesis thereof.

Our co-pending application Ser. No.10/396,107, now U.S. Pat. No. 6770,785 relates to the novel antioxidant based in functionalized hindered phenol obtained by the process of this invention.

BACKGROUND OF THE INVENTION

Diol containing pendant antioxidant and UV absorber groups are gaining much more importance to stabilize the polyurethane and polyesters against thermal and photochemical degradation. European Patent No. 627452 A1 and 627452 B1 disclose the preparation of diols with pendant UV absorber moiety and also the preparation of polyurethane and polyesters from diols containing pendant UV absorbing group.

Most thermoplastic polymers and coating compositions are unstable to the extended exposure to heat and ultraviolet light source in atmosphere. Thermoplastics and coatings tend to demonstrate unwanted colour changes and reduced mechanical strength upon exposure to UV and thermal radiation. The preliminary effect of ultraviolet radiation on polymers is the formation of free radicals on the polymer chain, which react with atmospheric oxygen to generate peroxide groups. Furthermore, the decomposition of peroxide group leads to chain scission and formation of carbonyl groups. Irradiation in absence of oxygen causes the increase in crosslinking. Ultimately, this reflects on the mechanical properties and the colour of the polymeric materials. In order to prevent or at least retard the damage caused by these factors, stabilizers are added to the plastics.

Antioxidants are the compounds, which upon addition to the polymers are capable of preventing or retarding the reactions of degradation caused by heat and light energy in presence of oxygen. 2,6-di-tertbutyl-p-cresol is the one of the most important antioxidants, which is used commercially. There are many patents about the preparation and use of functional antioxidant in polymers and coatings viz. U.S. Pat. No. 4677154, JP5001285A2, JP6198825A2, JP6025663A2, U.S. Pat. No. 5449715, and U.S. Pat. No. 6262323.

T. Narayan and I.Grosse, U.S. Pat. No. 4677154, Jun. 30, 1987 disclose a stabilizer package for polyurethane comprising a substituted cresol and another costabilizer. This disclosure relates to elimination of discoloration in polyurethanes, particularly thermoplastic polyurethanes by the addition to the reaction mixture from 0.01 to 1 percent by weight, based on the isocyanate component, a stabilizer package characterized as BHT and a compound selected from tris(nonylphenyl) phosphite, tetrakis(2,4-di-t-butylphenyl)-4,4'-biphenylene diphosphonite, bis(2,4-di-t-butylphenyl)pentaerythritol diphosphite, 2,2'-oxamido-bis[ethyl-3(3,5-dit-butyl-4-hydroxyphenyl)]propionate, disteryl thiodipropionate, triisodecyl phosphite, trilauryl trithiophosphite, distearyl pentaerythritol, 2,2'-ethylene bis (4,6-di-tertiarylbutylphenol), octadecyl 3-(3',5'-di-t-butyl-4'-hydroxy phenyl)propionate, 4,4'-thio-bis(2-t-butyl-5-methylphenol), 4,4'-thio-bis(2-t-butyl-5-methylphenol), 2,2'-methylene-bis-(4-methyl-6-t-butylphenol), tris(3,5-di-t-butyl-4-hydroxybenzyl)isocyanurate, phenothiazine, tris(2, 4-di-t-butylphenyl)phosphite, 4,4'-methylene bis(2,6-di-t-butylphenol), 2,6-di-t-butyldimethyl-aminomethylphenol and blends thereof.

Y. SUEMATSU, K. YAMAMOTO, JP5001285A2, Jan. 8, 1993 discloses the production of natural antioxidant. According to this disclosure, the process results in a natural antioxidant which gives an oxidation resistance equivalent to that given by well-known synthetic antioxidants such as BHA or BHT. Various parts of a sunflower, including flowers, leaves, stems, and roots, dried with hot air, crushed on an ultracentrifuge, and extracted with an org. common solvent such as hexane or ethyl ether. The resulting extract is concentrated under a reduced pressure, giving a natural antioxidant.

T. OKINA, K. KATO, H. SUZUKI, JP6198825A2, Jul. 19, 1994 discloses a composite structure of halogen-containing resin and polyurethane resin. The composite structure of this disclosure consists of a halogen-containing resin molded object (part) and the polyurethane resin molded object (part) coming into contact with or coming close to the halogen-containing molded object (part), 0.01–20 pts. wt. of an oxidation inhibitor is contained in the polyurethane resin compsn. at the time of the molding of the polyurethane resin molded object with respect to 100 pts. wt. of polyol contained in the polyurethane resin compsn. This oxidation inhibitor is composed of at least one of a phenolic oxidation inhibitor (BHT, BHA), a phosphorous oxidation inhibitor and a sulfur oxidation inhibitor.

A. NISHINA, S. HASHIMOTO, JP6025663A2, Feb. 1, 1994 discloses an antioxidant obtained by using torachrysone represented by a specified formula as an effective component. This antioxidant contains torachrysone of the formula as an effective component. Torachrysone (1,8-dihydroxy-2-acetyl-3-methyl-6-methoxynaphthalene) is prepared by purifying an extract from the seed of cassia tora L. or a herb such as Rheirhizoma. This antioxidant is used in an amount of 10–10000 ppm (in terms of torachrysone) based on the objective substance, e.g. food, cosmetic or medicine. It may be optionally used in combination with another additive such as tocopherol. It has an antioxidant power much stronger than that of a natural antioxidant such as tocopherol or L-ascorbic acid or a synthetic antioxidant such as BHA or BHT.

K. Plochocka et al., U.S. Pat. No. 5449715, Sep. 12, 1995 discloses a colorless, non-toxic, stabilized aqueous solution of a C1–C5 alkyl vinyl ether and maleic acid copolymers. The product comprises a colorless, stabilized aqueous solution of a C1–C5 alkyl vinyl ether and maleic acid copolymer which includes about 100 to 1,000 ppm of an additive mixture of (a) about 30–70% by weight of ethylenediaminetetraacetic acid (EDTA) or its salts, such as the disodium, trisodium, tetrasodium or disodium-calcium salts, and (b) about 30–70% by weight of a secondary additive which is an organic antioxidant and/or free radical scavenger selected from t-butylhydroquinone, propyl gallate, butylated hydroxy-anisole (BHA), butylated hydroxy-toluene (BHT), 4-hydroxymethyl-2,6-di-tert-butylphenol, 2,4,5-trihydroxy-butyrophenone (THBP) and N,N-diethylhydroxylamine, said stabilized solution exhibiting a retention of at least about 85–90% of its original viscosity after 3 months. Preferably, the solution is prepared by hydrolyzing the corresponding anhydride in the presence of said additive mixture.

Elder, Sherri et al., U.S. Pat. No. 6262323, Jul. 17, 2001 discloses polymerization inhibition of isoprene. In one preferred embodiment, the polymerization inhibiting composition includes phenylenediamine (PDA), butylated hydroxytoluene (BHT) and N,N'-diethylhydroxylamine (DEHA).

Monomeric and low molecular weight antioxidants are having limitation to their utility owing to their properties of migration and leaching. This phenomenon could lead to uneven distribution of antioxidants within the polymeric matrix. Leaching could be even more harmful as the loss of antioxidants from the polymer matrix could lead to extensive thermal and photo-degradation of the substrate. Therefore, in order to prevent the phenomena of migration and leaching, the antioxidants with polymerizing ability are being developed. This particular class of stabilizers would have even distribution within the polymer matrix and also they overcome the phenomena of migration and leaching.

OBJECTS OF THE INVENTION

The objective of the present invention is therefore, to provide a novel polycondensable diol functionalized antioxidant and the process for the preparation thereof which can fulfill the above-mentioned prerequisites of a stabilizer.

SUMMARY OF THE INVENTION

The present invention provides a novel diol functionalized antioxidant of formula I

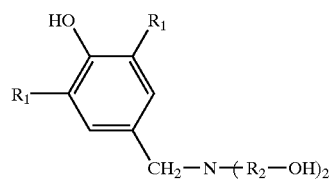

Formula I wherein $R_1$ is tert-butyl and $R_2$ is $C_1$ to $C_8$ linear or branched alkyl.

The present invention also provides process for the preparation of diol-functionalized antioxidant of the formula I:

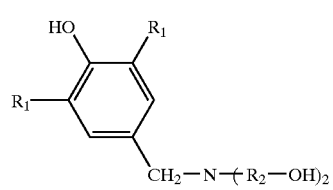

Formula I wherein $R_1$ is tert-butyl and $R_2$ is $C_1$ to $C_8$ linear or branched alkyl which comprises of dissolving a compound of formula III:

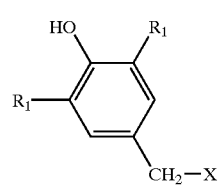

Formula III wherein $R_1$ is a tertiary butyl group and X is hydrogen, in a dry solvent adding drop-wise solution of bromine in dry carbon tetrachloride, maintaining reaction mixture at a temperature in the range of 80–85° C. under inert condition for a span of 4–5 hours, cooling the reaction mixture to room temperature and evaporating the solvent to obtain the brominated hindered phenol in the form of a viscous pale yellow liquid, of formula II:

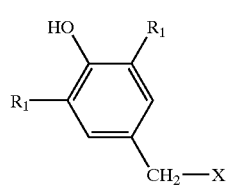

Formula II wherein $R_1$ is a tertiary butyl group and X is Br, reacting the solution of compound of formula II with a diol of formula IV:

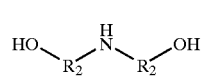

Formula IV wherein $R_2$ is $C_1$ to $C_8$ linear or branched alkyl along with an inorganic mild base under continuous stirring, refluxing the reaction mixture at a temperature in the range of 85–90° C. for 4–6 hrs to obtain fine crystals of the diol functionalized antioxidant of formula (I).

In one of the embodiments of the present invention, the neutral organic solvent used for dissolving the compound having formula (III) is selected from chlorinated solvent like, carbon tetrachloride, chloroform, chlorobenzene and dichloromethane.

In another embodiments the bromination of compound of formula (III) is achieved by using liquid bromine.

In still another embodiment the organic solvent selected for dissolving the compound having general formula (II) is selected from benzene, toluene, xylene, carbon tetrachloride, dichloromethane and tetrahydrofuran.

In still another embodiment the diol is selected from $C_1$ to $C_8$ linear or branched alkyl ethanolamine.

In still another embodiment the mild inorganic base is selected from carbonates and bi-carbonates of alkali metals such as potassium carbonate, sodium carbonate, calcium carbonate, sodium bicarbonate and potassium bicarbonate.

DETAILED DESCRIPTION OF THE INVENTION

The present invention also provides process for the preparation of diol-functionalized antioxidant which comprises of dissolving a compound of formula III:

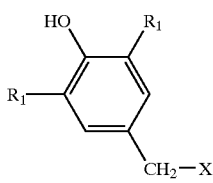

Formula III wherein $R_1$ is a tertiary butyl group and X is hydrogen, in a dry solvent adding drop-wise solution of bromine in dry carbon tetrachloride, maintaining reaction mixture at a temperature in the range of 80–85° C. under inert condition for a span of 4–5 hours, cooling the reaction mixture to room temperature and evaporating the solvent to obtain the brominated hindered phenol in the form of a viscous pale yellow liquid, of formula II:

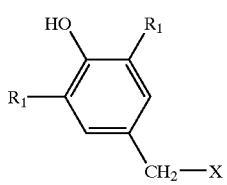

Formula (II)

wherein $R_1$ is a tertiary butyl group and X is Br, reacting the solution of compound of formula (II) with a diol of general formula (IV):

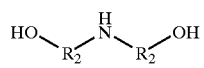

Formula IV wherein $R_2$ is $C_1$ to $C_8$ linear or branched alkyl along with an inorganic mild base under continuous stirring, refluxing the reaction mixture at a temperature in the range of 85–90° C. for 4–6 hrs to obtain fine crystals of the diol functionalized antioxidant of formula (I).

The neutral organic solvent used for dissolving the compound having formula (III) is selected from chlorinated solvent like, carbon tetrachloride, chloroform, chloroben- zene and dichloromethane. The bromination of compound of formula (III) is preferably achieved by using liquid bromine.

The organic solvent selected for dissolving the compound having general formula (II) is selected from benzene, toluene, xylene, carbon tetrachloride, dichloromethane and tetrahydrofuran. The diol itself is preferably selected from $C_1$ to $C_8$ linear or branched alkyl ethanolamine.

The mild inorganic base is selected from carbonates and bi-carbonates of alkali metals such as potassium carbonate, sodium carbonate, calcium carbonate, sodium bicarbonate and potassium bicarbonate.

The following examples describe the process for the preparation of the diol-functionalized antioxidants, which are illustrative only and should not be constructed, to the scope of the present invention in any manner.

EXAMPLE 1

Synthesis of 3,5-di-tert-butyl-4-hydroxy Benzyl Bromide 3,5-di-tert-butyl-4-hydroxy benzyl bromide was prepared from the bromination of 2,6-di-tert-butyl-4-methyl phenol. In a 250 ml three-necked round bottomed flask, 2.5 gm of 2,6-di-tert-butyl-4-methyl phenol and dissolved in 25 ml of dry carbon tetrachloride. In a separate conical flask, 0.3 ml of bromine was dissolved in 25 ml of dry carbon tetrachloride and solution was transferred to a cylindrical funnel with pressure equalizing tube. Three-necked round-bottomed flask containing solution of 2,6-di-tert-butyl-4-methyl phenol was kept in oil-bath at 85° C. Nitrogen was bubbled through the solution for creating inert atmosphere. Cylindrical funnel containing bromine solution was mounted on the three-necked round-bottomed flask. Solution in the flask was continuously stirred with the help of magnetic stirrer. Bromine solution was added, drop-by-drop, from funnel to the flask for a span of 4–5 hours till all the solution was poured out. After that heating was stopped and the final reaction mixture was allowed to cool at room temperature. Finally the product obtained was a viscous yellow liquid and was absolutely pure. The yield of 3,5-di-tert-butyl-4-hydroxy benzyl bromide was 3.03 gm (90%)

EXAMPLE 2

Synthesis of 2,6-di-tert-butyl-4-(bis(2-hydroxyethyl) aminomethyl)phenol

In a round bottom flask taken 2.24 gm of 3,5-ditertbutyl-4-hydroxy benzyl bromide and 0.6 ml of N, N-diethanol amine and dissolved in 100 mL of benzene. The reaction mixture was refluxed with constant stirring at 75–80° C. for 6 hrs. The product was crystallized out in the form of colorless needles. The solvent was decanted, crystals were filtered off and washed with pure benzene. The yield of the product is 1.43 gm (64%). Product was identified by $^1$H-NMR and FT-IR spectroscopic techniques.

EXAMPLE 3

Synthesis of 2,6-di-tert-butyl-4-(bis(2-hydroxy isopropyl)aminomethyl) phenol

In a round bottom flask taken 2.5 gm of 3,5-di-tert-butyl-4-hydroxy benzyl bromide and 0.8 ml of N, N-diisopropanol amine and dissolved in 100 mL of benzene. The reaction mixture was refluxed with constant stirring at 75–80° C. for 6 hrs. The product crystallized out in form of colorless needles. The solvent was decanted, crystals were filtered off and washed with pure benzene. The yield of the product is 2.06 gm (68%). Product was identified by $^1$H NMR and FT-IR spectroscopic techniques.

The Process of the Present Invention has Four Distinct Merits:

1) The process is highly economic.
2) The process comprises of commonly available organic reagents and mild reaction conditions.
3) High yield ($\geq$65%) can be achieved very easily.
4) The process involves synthesis of novel diol-functionalized antioxidants from readily available conventional hindered phenols by very short and facile route with simple via moderate reaction conditions.

We claim:

1. A diol functionalized antioxidant which is 2,6-di-tert-butyl-4-(bis(2-hydroxy isopropyl)aminomethyl)phenol.

2. A process for the preparation of diol-functionalized antioxidant of the formula I below:

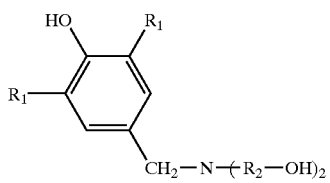

wherein R1 is tert-butyl and R2 is selected from the group consisting of C1 to C8 linear or branched alkyl, said process comprising dissolving a compound formula III:

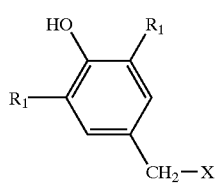

Formula III wherein R1 is a tertiary butyl group and X is hydrogen in a dry solvent, adding dropwise a solution of bromine in dry carbon tetrachloride or liquid bromine maintaining reaction mixture at a temperature in the range of 80–85° C. under inert condition for a span of 4–5 hours, cooling the reaction mixture to room temperature and evaporating the solvent to obtain a hindered phenol of formula II in the form of a viscous, pale yellow liquid,

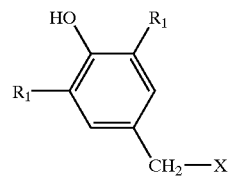

Formula II wherein $R_1$ is a tertiary butyl group and X is Br, and dissolving the compound of formula II in an organic solvent, reacting the solution of compound of formula II with a diol of general formula IV:

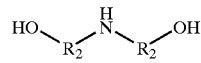

Formula IV wherein $R_2$ is selected from the group consisting of C1 to $C_8$ linear or branched alkyl, along with an inorganic mild base under continuous stirring, refluxing the reaction mixture at a temperature in the range of 85–90° C. for 4–6 hrs to obtain fine crystals of the diol functionalized antioxidant of formula (I).

3. A process as claimed in claim 2 wherein the dry solvent used for dissolving compound of formula III is a chlorinated solvent.

4. A process as claimed in claim 3 wherein the chlorinated solvent is selected from the group consisting of carbon tetrachloride, chloroform, chlorobenzene and dichloromethane.

5. A process as claimed in claim 2 wherein the bromination of compound of formula (III) is carried out using liquid bromine.

6. A process as claimed in claim 2 wherein the organic solvent selected for dissolving the compound of formula II is selected from the group consisting of benzene, toluene, xylene, carbon tetrachloride, dichloromethane and tetrahydrofuran.

7. A process as claimed in 2 wherein the diol is selected from $C_1$ and $C_3$ to $C_8$ linear or branched alkyl ethanolamine.

8. A process as claimed in claim 2 wherein the mild inorganic base is selected from carbonates and bi-carbonates of alkali metals.

9. A process as claimed in claim 8 wherein the carbonates and bicarbonates of alkali metals are selected from the group consisting of potassium carbonate, sodium carbonate, calcium carbonate, sodium bicarbonate and potassium bicarbonate.

* * * * *